United States Patent [19]

Moody

[11] Patent Number: 4,655,206

[45] Date of Patent: Apr. 7, 1987

[54] SPINAL RESTRAINT

[76] Inventor: Brian Moody, 1619 16th La., Lake Worth, Fla. 33463

[21] Appl. No.: 585,848

[22] Filed: Mar. 2, 1984

[51] Int. Cl.[4] .......................... A61F 13/12; A61G 1/00

[52] U.S. Cl. ...................................... 128/134; 5/82 R

[58] Field of Search ..................... 128/134, 133, 87 R, 128/78; 5/82 R

[56] References Cited

U.S. PATENT DOCUMENTS

| | | | |
|---|---|---|---|
| Re. 28,916 | 7/1976 | Rice et al. | 5/83 |
| 787,848 | 4/1905 | Lung | 5/82 |
| 2,033,779 | 3/1936 | Monk | 5/82 |
| 2,192,821 | 3/1940 | Torines | 5/83 |
| 2,409,934 | 10/1946 | Haggard et al. | 5/82 |
| 2,675,564 | 4/1954 | Hughes | 5/82 |
| 3,151,343 | 10/1964 | McCormick | 5/82 |
| 3,707,734 | 1/1973 | Matthews | 5/82 |
| 3,889,668 | 6/1975 | Ochs et al. | 5/82 |
| 3,897,778 | 8/1975 | Forbes-Robinson et al. | 5/83 |
| 4,034,748 | 7/1977 | Winner | 5/82 |
| 4,058,112 | 11/1977 | Johnson | 128/133 |
| 4,064,574 | 12/1977 | Schnitzler | 5/82 |
| 4,124,908 | 11/1978 | Burns et al. | 5/82 |
| 4,127,120 | 11/1978 | Applegate | 5/82 |
| 4,151,842 | 5/1979 | Miller | 128/87 |
| 4,283,068 | 8/1981 | Keyser | 5/82 |
| 4,369,982 | 1/1983 | Hein et al. | 5/82 |
| 4,400,820 | 8/1983 | O'Dell et al. | 128/134 |
| 4,451,932 | 6/1984 | Wagemann et al. | 128/133 |

OTHER PUBLICATIONS

"Jems", Feb. 1983, pp. 37–43.

*Primary Examiner*—William R. Dixon, Jr.

*Assistant Examiner*—Karl Group

*Attorney, Agent, or Firm*—Steele, Gould & Fried

[57] ABSTRACT

A spinal restraint includes a rigid board and a flat, elongated strap for tying a patient to the board. The strap includes means for attachment to the board on both ends of the strap and is length-adjustable. The board has a spacer which holds the board slightly above a flat surface upon which it is placed. The patient is quickly and securely tied to the board by lacing the strap from side to side over the patient, progressively placing portions of the strap into diagonal slots extending inwards from the periphery of the board. The strap or straps is ultimately secured at the patient's shoulders. At the shoulders the strap is placed over portions of a head restraint pad extending onto the patient's shoulders. The system, including the board, strap and head restraint is length-adjustable to accommodate patients of various sizes.

16 Claims, 5 Drawing Figures

SPINAL RESTRAINT

BACKGROUND OF THE INVENTION

1. Field of the Invention

The invention relates to the field of spinal restraints for treatment of humans, and particularly to spinal restraints adapted for emergency and rescue operations.

2. Description of the Prior Art

Spinal restraint boards, rescue boards, stretchers and the like are known in a variety of embodiments. The general function of such apparatus is to support an injured person during transport to a point of further processing. For example, victims of automobile accidents, soldiers injured in battle and victims of traumatic injury in general may be unable to transport themselves, at least without risk of further injury, and require a means of safe transportation to a place of medical treatment.

Victims or suspected victims of spinal injuries are especially vulnerable during transport. For example, a patient suffering from a broken neck or back may lack the necessary structural interconnection of vertebrae to limit displacement of body parts and to protect the spinal cord from traumatic injury during movement. Catastrophic traumatic injury can therefore occur to the spinal cord during transport, the patient possibly losing important body functions unnecessarily, becoming, for example, paraplegic or quadraplegic.

In order to deal with injuries to the cervical vertebrae and to deal with the danger of spinal cord injuries in general, the art has conceived of using relatively simple boards as stretchers, or in addition to stretchers, in order to maintain a predetermined relative position of a patient's body parts during transport. For injuries to cervical vertebrae, such restraint devices may be relatively short, for example, as shown in U.S. Pat. No. 4,127,120-Applegate or U.S. Pat. No. 4,034,748-Winner. These devices are adapted to engage and support the patient's torso and head, rather than to act as a complete stretcher. In U.S. Pat. No. 3,707,734-Matthews, a universal board is disclosed, operable as a full stretcher, or separable into parts for use as a torso board.

In each of the foregoing disclosures, the patient is held against the board by means of flat, relatively wide straps. Flat straps are comfortable in that they spread forces over a wider area, and may be made somewhat tighter than cylindrical or tubular laces, strings and ties. Most frequently, flat straps are adapted to pass perpendicularly across the torso or spinal board whereby they wrap smoothly over the sides of the board. In other words, the straps are attached near the edges of the board or wrapped around the edges of the board, and passed over the patient along a line perpendicular to an axis defined by the patient. In order to securely tighten the straps to hold the patient, such attachments must be length adjustable, for example, by means of a buckle or the like. Frequently, the straps resemble the usual garment-type belt having a buckle on one free end adapted to engage the other free end at one of a plurality of spaced holes.

A patient to be supported on a torso board or spine board is virtually always substantially smaller in width than the board. Accordingly, attachment of perpendicular straps at the edges of the board necessarily allows a certain amount of side-to-side movement of the patient even within the strap. Accordingly, such boards may be made narrow, frequently becoming progressively narrow towards the patient's feet and/or head. Another means of more closely restraining the patient is to run the straps diagonally over the patient, rather than perpendicularly with respect to the patient's axis. Straps running diagonally are necessarily more secure than straps running horizontally in that the straps exert an inward as well as a downward force on the patient with respect to the restraint board. Diagonal straps, however, are more complicated than perpendicular ones.

Examples of diagonal straps are shown in the aforesaid patent to Applegate, in which straps are looped around the patient and locked in holes in the board. In connection with narrow laces, string or rope, U.S. Pat. No. 3,151,343-McCormick also employs diagonal string lacing. In U.S. Pat. No. 4,283,068-Keyser, diagonal lacing is disclosed in connection with a resilient transport platform for game. U.S. Pat. No. 787,848-Lung teaches diagonal laces to close a blanket or bag over the victim.

In order to use a restraint system employing diagonal straps or laces according to the aforesaid patents, it is necessary to run the straps and/or laces through holes, hooks or like receptacles in the restraint board, the same being placed along the patient, for example, near the edges of the board. Alternatively, it is possible to use individual belts, which are connected over the patient using buckles. In any event, use of diagonal lacing requires either a plurality of relatively short inter-engageable lace or strap segments attached near the periphery of the board, or means for engaging intermediate portions of one or more long straps. In the event that long straps are employed, the user enjoys the benefit of fewer pieces, simpler storage and the like; however, lacing the ropes or straps through the holes in the torso board is quite slow. Moreover, lacing the straps through the board requires substantial free access to both the upper and lower surfaces of the board, necessitating either supporting the board well above the ground for attachment to the patient or repeatedly lifting the edges of the board, and possibly jarring the patient, in order to lace the patient down. Finally, the usual diagonal lacing as shown, for example, in McCormick, is not suitable for use with wide straps. Such straps will not lay flat unless they are passed diagonally from side to side across the board first above the patient, then across the board behind the patient, progressing helically around the patient and the board.

According to the present invention, diagonal straps are applied to a spinal board in a manner in which the straps are quickly and easily laced diagonally across the patient without the need to pass a strap under the patient or to otherwise jar the patient during the lacing procedure. Also according to the invention, the flat straps remain laying flat when routed through the progressive strap-engaging slots placed along the edges of the board.

The present invention also involves structure for applying the spine board to patients over a range of heights, including children and adults. The invention further involves a likewise universally applicable head restraint structure for protection of the cervical vertebrae. According to the invention, a pad in the general shape of an inverted "U" includes flaps at the ends of the inverted "U" legs, which flaps lay against the patient's shoulders when the head restraint is installed. The diagonal passage of flat straps attaching the patient to the restraint board further engage the head restraining mechanism, namely, at the shoulders, thereby restraining the head. The head restraint also includes means for engaging the board at or near the crown of the patient's head, and hook-and-pile fastened straps for engaging the patient's forehead and chin, the straps being attachable to the head restraint pad at a range of positions.

By virtue of the diagonal slots for attachment, the patient restraint system of the invention is very quickly installed and is at the same time very secure and comfortable. The generalized system also interacts with the head restraint, providing an optimum combination of convenience and effectiveness.

SUMMARY OF THE INVENTION

It is an object of the invention to attach an injured person securely to a rigid structural support.

It is also an object of the invention to provide a patient support which is safe and comfortable.

It is another object of the invention to attach the patient to the support as quickly as possible, and with a minimum possibility of exposing the patient to jarring or vibration which might cause further injury.

It is yet another object of the invention to provide a patient restraint which is inexpensive and convenient in its initial cost and in its use and storage.

It is still another object of the invention to achieve the maximum in convenience and minimum cost without drawback in the effectiveness of attachment and patient protection.

These and other objects are accomplished by a spinal restraint device including a rigid board and a flat, elongated strap for tying a patient to the board. The strap includes means for attachment to the board on both ends of the strap and is length-adjustable. The board comprises a spacer which holds the board slightly above a flat surface upon which it is placed. The patient is quickly and securely tied to the board by lacing the strap from side to side over the patient, progressively placing intermediate portions of the strap into diagonal slots extending inwards from the periphery of the board. The one or more straps is ultimately secured at the patient's shoulders. At the shoulders the strap is placed over portions of a head restraint pad extending onto the patient's shoulders. The system, including the board, strap and head restraint is length-adjustable to accommodate patients of various sizes.

BRIEF DESCRIPTION OF THE DRAWINGS

There are shown in the drawings the embodiments which are presently preferred. It should be understood, however, that the invention is not limited to the precise arrangements and instrumentalities shown in the drawings, wherein.

DETAILED DESCRIPTION OF THE PREFERRED EMBODIMENTS

Figure 1:
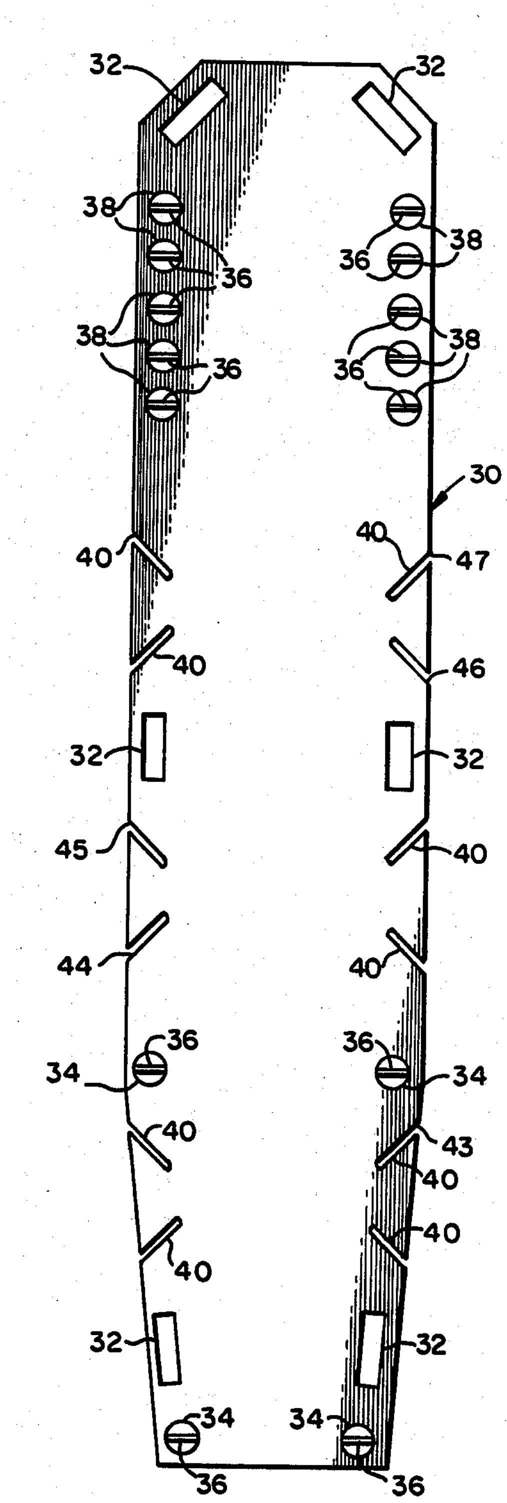
FIG. 1 is a plan view of a patient restraint board according to the invention.

The patient restraint board 30, shown in FIG. 1, provides the structural support for body parts which a patient suffering from a spinal injury is lacking. Normally, the structural interconnection of the patient's vertebrae protect the spinal cord from injury, hold the body parts within a range of positions, and resist any undue bending or shear forces. Should a vertebra or the connection between vertebrae become broken, the patient's body parts become free to move with respect to one another, causing possible injury to the now-unprotected spinal cord. This problem is acute with respect to the patient's cervical vertebrae, due to the fact that the patient's head is a relatively heavy portion of the body, and is rather weakly mounted in cantilevered fashion on the neck. Therefore, any injury to the neck exposes the patient to the danger of injury to the spinal cord at the neck, caused for example, by the patient's head rocking from side to side and causing shear forces between adjacent vertebrae.

The invention is likewise applicable to spinal injuries generally, and also to non-spinal injuries such as broken bones or unconsciousnes, in which it is important to restrain a patient for transport. The board of FIG. 1 includes means for tying the patient to the board, and also means for manipulating the board for transport. Board 30 is provided with handgrips or handholds 32 at each corner and at a central area. The handgrip holes are located near the edges of the board, such that the board and the patient attached thereto can be easily carried or manipulated. The patient is attached by means of straps, shown in FIG. 2, which are attached to the board at opposite ends of the straps, and passed diagonally across the patient through diagonal slots 40, the slots extending inward from the side of the board. A pair of spacers 48 support the board slightly above the surface on which the board rests, e.g., the ground. The straps remain flat due to the angles of the slots. Inasmuch as the slots are completely accessible to engage intermediate portions of the strap at the edges of the board, the user need not lace the ends of the straps through holes or wrap them around the board, either of which requires substantial freedom of access to opposite sides of the holes. Instead, intermediate portions of the strap are looped and wrapped around a cleat defined by neighboring diagonal slots at the board edges. The ends of the strap are attached, for example, by means of spring clips engaging rods 36 which extend through connection holes 34 at the head and feet.

In order to accommodate patients of different sizes, connection holes 34, including pins 36, are provided at least at one point spaced from the extreme bottom of the board. Moreover, in order to accomplish the precise and secure attachment of a head restraint pad, a series of closely spaced connection holes 38 and pins 36 are provided at the head end of the board.

With reference to FIG. 1, the diagonal slots 40 are disposed such that the flat strap is positioned to run diagonally across the patient. Each pass of the strap is directed, without wrinkling, from side to side diagonally across the patient progressing upwards (or downwards). For example, the strap may be attached to the board by a first end by a clip hooked at the lower left attachment hole 34, then routed over the patient's feet to slot 42, along the back side of the board to slot 43, then diagonally across the patient to slot 44, followed by slot 45, 46, 47, and terminating finally at one of the head restraint connection holes 38. At hole 38, the opposite end of the strap is attached, for example, by means of another hook or spring clip.

Figure 2:
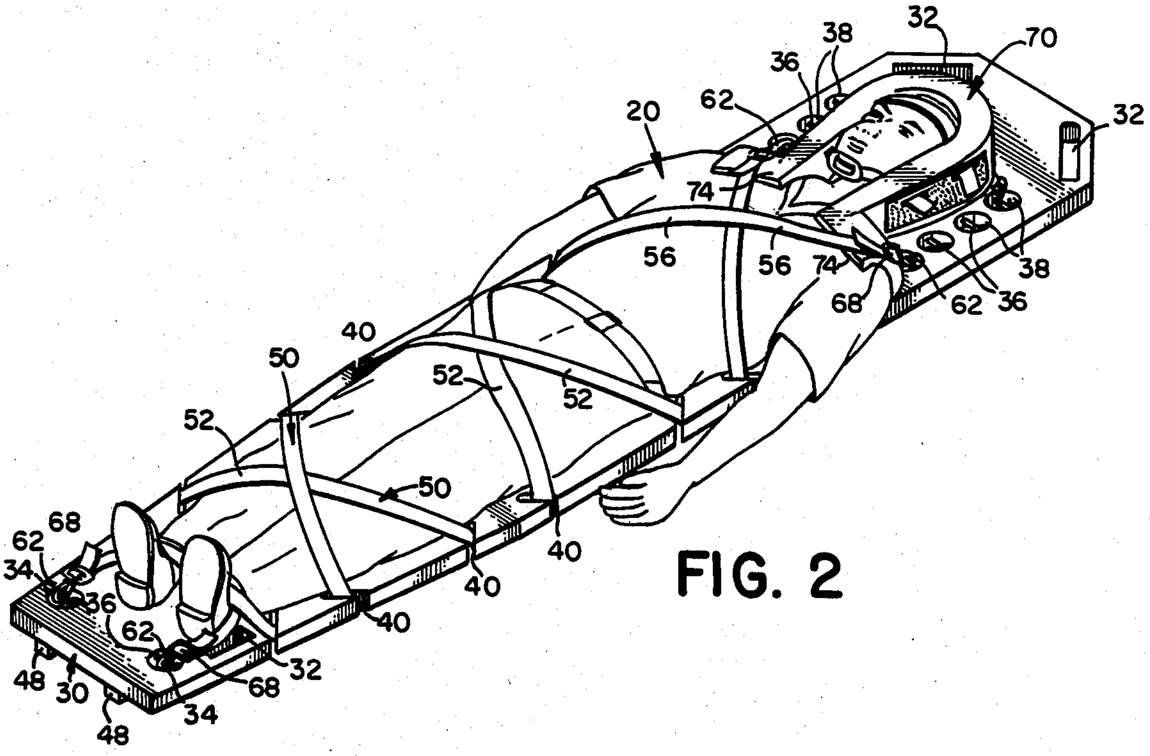
FIG. 2 is a perspective view of the complete patient restraint apparatus, applied to a patient.

The restraint system is shown carrying a patient in FIG. 2. Two straps 50 are shown, each attached by a first end to one of holes 34, and by a second end to one of holes 38, progressing diagonally across the patient through diagonal slots 40. The ends of straps 50 are preferably attached at the connection holes 34 by means of spring clips 62. Means for shortening the strap are also provided, for example, by use of buckle 68.

The passage of straps 50 across patient 20 and around board 30 serves to hold the patient downwards against board 30. Moreover, the diagonal passage of the straps serves further to position the patient at the axial center of board 30, providing an inward force against movement toward the sides of the board, which force is not present in simple horizontal straps. Finally, the final diagonal traverse 56 of straps 50, passing over the patient's shoulders, engages an interfitting head restraint mechanism 70, thereby fully supporting the patient body parts from head to foot.

Head restraint 70 comprises a section of resilient pad which is wrapped over the crown of the patient's head into the shape of an inverted "U". Adjacent the patient's shoulders, flaps extend from the pad, to lay over the patient's shoulders, particularly near the neck. Accordingly, the final diagonal passage 56 of strap 50 engages the head restraint flap 74.

Figure 3:
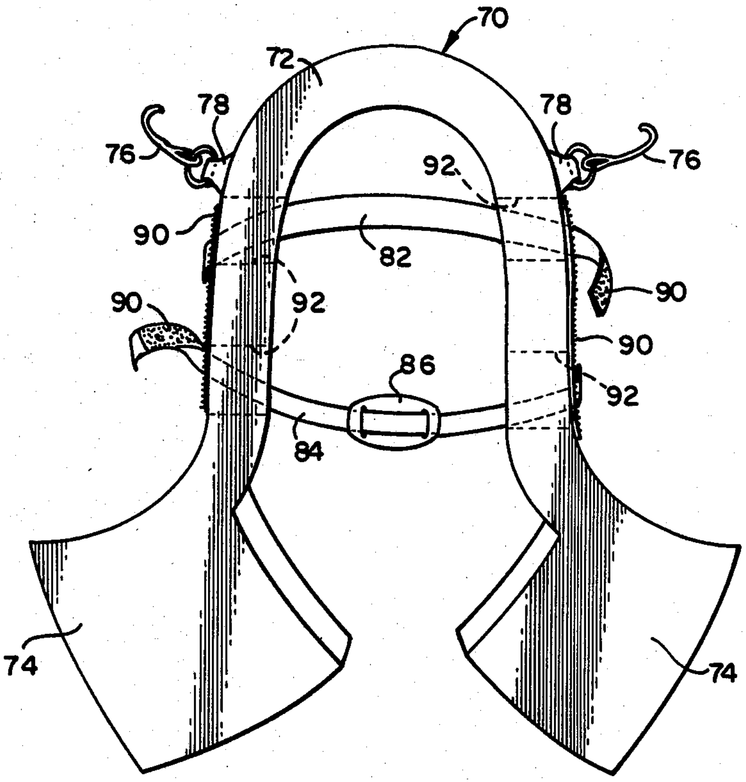
FIG. 3 is a top plan view of the head restraint of the invention.

In FIG. 3, the head restraint is shown in approximately the position it occupies in use. The inverted "U" section 72 is placed over the patient's head and restraining straps 82, 84, for the forehead and chin, respectively, pull the sides of "U" section 72 toward one another along the sides of the patient's head. Meanwhile, straps 50 pull the "U" section 72 downward on the patient's head by means of force applied at the shoulders, on flap 74. Attachment hooks 76 are provided near the patient's crown on "U" section 72. Hooks 76 are preferably connected to an embedded reinforcement member 78, for example, a strip of aluminum embedded within the head restraint pad 70, connecting hooks 76 on opposite sides of the patient. Hooks 76 engage pins in head restraint holes 38, which are provided along a range of connection, to accommodate patients of various sizes.

Forehead and chin straps 82, 84, are preferably provided with loop-and-pile fastener pads 90 at their ends, interacting with loop-and-pile fastener pads provided over an enlarged area along the sides of the head restraint pads 70. Straps 82, 84 pass through oversized slots 92 in the sides of the head restraint pad, whereby the loop-and-pile fasteners 90 on the strap and head restraint pad, respectively, may be affixed to one another at any of a range of lengths and angles. For example, it is frequently desirable to exert a force against the patient's chin by means of chin strap 84, thereby tending to hold the head within the inverted "U" 72. A chin-engaging member 86 may be provided in order to assist in the upward force, and to prevent strap 84 from resting across the patient's neck.

Figure 5:
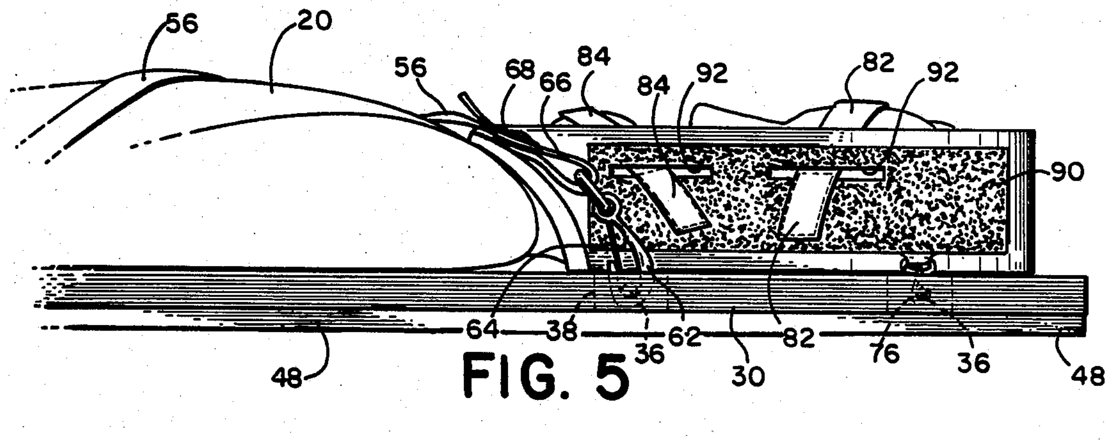
FIG. 5 is a partial elevation view of the patient restraint, as shown in FIG. 2.

The connection of the head restraint and board is shown in detail in FIG. 5. Upper diagonal traverses 56 of the straps pass over shoulder flap 74, and are attached to connection holes 38 at pins 36. The straps are preferably length adjustable by means of adjusting the dimensions of the end loop 66 on the strap, for example, by means of buckle 68. Spring clips 62 comprise a hook portion of rigid material, resiliently closed by a spring 64. The spring may be pushed back to expose the hook in installing the spring clip.

Head reastraint hooks 76 may also include springs, or the inherent resilience of pad 70 can be employed to provide an upward force tending to keep hook 76 on its associated pin 36.

Hook-and-pile fastener 90, as well as the strap slots 92, are substantially oversized. In this respect, the straps 82, 84 can be adjusted over a wide range as required for the particular patient. The device is therefore applicable to a wide range of patient sizes and proportions.

Figure 4:
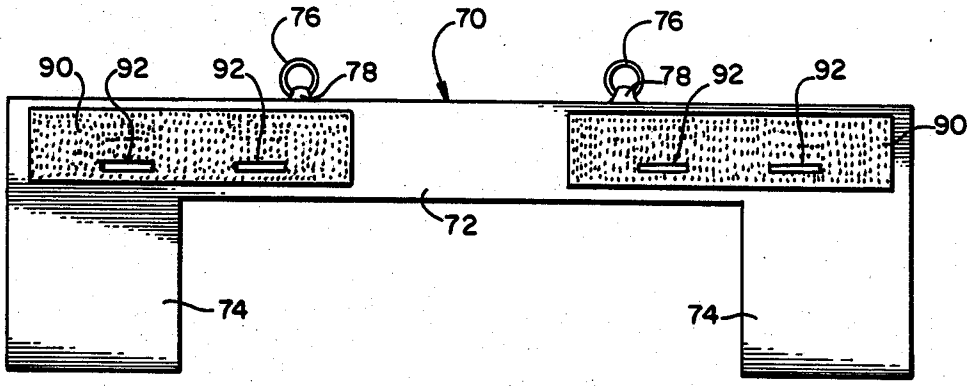
FIG. 4 is an elevation view of the head restraint, extended for storage.

The head restraint pad can be opened for purposes of storage, as shown in FIG. 4. Reinforcement 78, which is embedded in the pad material between connecting apparatus 76, can be made resilient, for example, spring steel, or deformable, for example, aluminum sheet, in either event serving to stiffen and better anchor the head restraint pad at the patient's crown.

The device of the invention is likewise applicable to torso boards, that is, boards adapted to extend from above the patient's head to some point along the lumbar region or legs. The invention is also applicable to patient restraint systems of other types.

The invention having been disclosed, additional variations will now occur to persons skilled in the art. Reference should be made to the appended claims rather than the foregoing specification as representing the true scope of the invention.

What is claimed is:

1. An apparatus for restraining a patient, comprising:

A rigid board and a flat, elongated strap for typing the patient to the board, the board having openings at opposite ends thereof with pins being disposed across said openings, the board having a plurality of slots at spaced points between said means for engaging the opposite ends, the slots being at least as long as the strap is wide, the slots extending inwards from peripheral, opposite side edges of the board and the slots opening at the peripheral edges of the board, the slots being angled at about forty-five degrees with respect to an axis of the board and consecutive slots along the edges being substantially perpendicular, whereby the patient may be quickly tied to the board by passing portions of the strap intermediate the opposite ends into the slots from the peripheral edges.

2. The apparatus according to claim 1, wherein slots on alternating sides of the board progressing along an axis defined by the board are parallel, whereby the slots hold the strap flat over the patient when tied to the board.

3. The apparatus of claim 1, further comprising at least one spacer on a side of the board opposite the patient, the spacer holding the board above a support surface for access to the slots.

4. An apparatus for restraining a patient, comprising:

a board having openings at opposite ends thereof, pins being disposed across the openings, the board having a plurality of diagonal slots extending inward from opposite side edges of the board, the slots opening at the side edges of the board and defining a lacing path progressing from side to side and from end to end along the board, the slots being angled at about forty-five degrees with respect to an axis of the board and consecutive slots along the edges being substantially perpendicular;

means to space the slots from a surface upon which the board is placed;

an elongated strap having fittings on each end adapted to engage the pins, the strap being flat and dimensioned to fit the slot; and, means for adjusting the length of the strap.

5. The apparatus according to claim 4, wherein the board has a series of spaced openings having pins at one of the opposite ends, whereby patients of various sizes can be accommodated.

6. The apparatus according to claim 5, wherein the slots are spaced to position the strap at spaced traverses across the patient, the straps being attachable to the pins immediately adjacent the patient's shoulders.

7. The apparatus according to claim 6, further comprising a head restraint defining a receptacle for engaging the patient's head, the head restraint having side portions adapted to extend along opposite sides of the patients head, and end portions attached to the side portions and extending perpendicular outwards from the side portions, the end portions adapted to engage the patient's shoulders.

8. The apparatus according to claim 7, wherein the strap is attachable over the end portions, whereby the straps restrains the patient's head and shoulders against movement relative to the board and relative to one another.

9. The apparatus according to claim 8, wherein the head restraint comprises a pad in the shape of an inverted "U", the pad extending along the sides and top of the patient's head.

10. The apparatus according to claim 9, wherein the pad extends over the patient's shoulders and is held on the shoulders by the strap.

11. The apparatus according to claim 7, further comprising at least one transverse strap adjustably attached to the head restraint at opposite sides of the patient's head, the transverse strap urging the head restraint against the sides of the patient's head.

12. The apparatus according to claim 11, wherein the transverse strap comprises at least one of a forehead strap and a chip strap adapted to fit against the patient's forehead and chin respectively.

13. The apparatus according to claim 11, further comprising hook-and-pile fasteners on the strap and head restraint for adjusting at least one of the length and angular positions of the transverse strap.

14. The apparatus according to claim 13, further comprising reinforcing means embedded in the head restraint and engagement devices attached to the reinforcing means and attachable to the board.

15. A patient restraint apparatus, comprising:

a spine board to be tied against the patient's back, the board having a plurality of slots extending inward from opposite side edges of the board, the slots opening at the opposite side edges, the slots being angled at about forty-five degrees with respect to an axis of the board and consecutive slots along the edges being substantially perpendicular to one another, the board having openings at opposite ends thereof with pins being disposed across said openings;

a strap having hooks at each end and a means for shortening the straps intermediate the hooks, the strap being flat and dimensioned to fill the slots; and, a head restraint pad partially enclosing the patient's head and shoulders, the pad being engaged by the strap at the patients shoulders.

16. The apparatus according to claim 15, comprising a pair of straps, the slots being disposed on opposite sides of the board to positions the straps in a plurality of parallel and perpendicular traverses across the patient, the traverses being diagonal with respect to the axis.

* * * * *